(12) United States Patent
Harttig et al.

(10) Patent No.: US 8,999,235 B2
(45) Date of Patent: Apr. 7, 2015

(54) METHOD AND STERILIZING DEVICE FOR STERILIZING AN IMPLANTABLE SENSOR

(71) Applicant: Roche Diagnostics Operations, Inc., Indianapolis, IN (US)

(72) Inventors: Herbert Harttig, Neustadt (DE); Ralf Heinrich, Schwegenheim (DE); Stefan Konig, Lorsch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 185 days.

(21) Appl. No.: 13/667,778

(22) Filed: Nov. 2, 2012

(65) Prior Publication Data
US 2013/0137950 A1 May 30, 2013

(30) Foreign Application Priority Data
Nov. 30, 2011 (EP) .................................. 11191283

(51) Int. Cl.
*A61L 2/00* (2006.01)
*G01N 23/00* (2006.01)
(Continued)

(52) U.S. Cl.
CPC ........... *A61B 5/1473* (2013.01); *A61B 5/14532* (2013.01); *A61B 5/14865* (2013.01); *A61L 2/087* (2013.01)

(58) Field of Classification Search
CPC .................................. A61L 2/00; A61L 12/00
USPC .................. 422/1, 22, 24; 250/455.11, 492.1, 250/492.3, 506.1, 515.1; 604/199
See application file for complete search history.

(56) References Cited

U.S. PATENT DOCUMENTS

| 5,496,302 A | 3/1996 | Minshall et al. |
| 6,360,888 B1 | 3/2002 | McIvor et al. |

(Continued)

FOREIGN PATENT DOCUMENTS

| DE | 10 2004 033 219 A1 | 2/2006 | |
| WO | WO 2006/005503 A1 * | 1/2006 | ............... A61B 5/15 |

OTHER PUBLICATIONS

Demtröder, W.; Experimentalphysik 4, Kem-, Teilchen—und Astrophysik; 1995, 1999, 2004, 2006, 2010; pp. 91, 92; Springer; Dordrecht NE, Heidelberg DE, London UK, New York.

*Primary Examiner* — Monzer R Chorbaji
(74) *Attorney, Agent, or Firm* — Bose McKinney & Evans LLP

(57) ABSTRACT

A method for sterilizing an implantable sensor for sensing an analyte in a body tissue. The implantable sensor has a sensor part which can be introduced into the body tissue, at least one sensor electrode for sensing the analyte, and at least one electronics part. The electronics part has at least one electronic component and is connected to the sensor part. The method includes (a) introducing the implantable sensor into a package, the package sealing the implantable sensor from bacteria and accommodating a radiation shield, (b) irradiating the implantable sensor in the package with sterilizing radiation from at least one irradiating direction, in particular with electron radiation, the radiation shield shielding the electronic component of the electronics part from the sterilizing radiation, the radiation shield being arranged in such a way that the sensor part is sterilized by the sterilizing radiation.

33 Claims, 4 Drawing Sheets

(51) Int. Cl.
*A61N 5/00* (2006.01)
*G21F 5/00* (2006.01)
*A61M 5/32* (2006.01)
*A61B 5/1473* (2006.01)
*A61B 5/145* (2006.01)
*A61B 5/1486* (2006.01)
*A61L 2/08* (2006.01)

(56) References Cited

U.S. PATENT DOCUMENTS

| | | |
|---|---|---|
| 6,594,156 B1 | 7/2003 | Van Antwerp et al. |
| 2008/0242962 A1 | 10/2008 | Roesicke et al. |
| 2008/0255440 A1 | 10/2008 | Eilersen et al. |
| 2009/0257911 A1 | 10/2009 | Thomas et al. |
| 2011/0152644 A1 | 6/2011 | Heck et al. |

\* cited by examiner

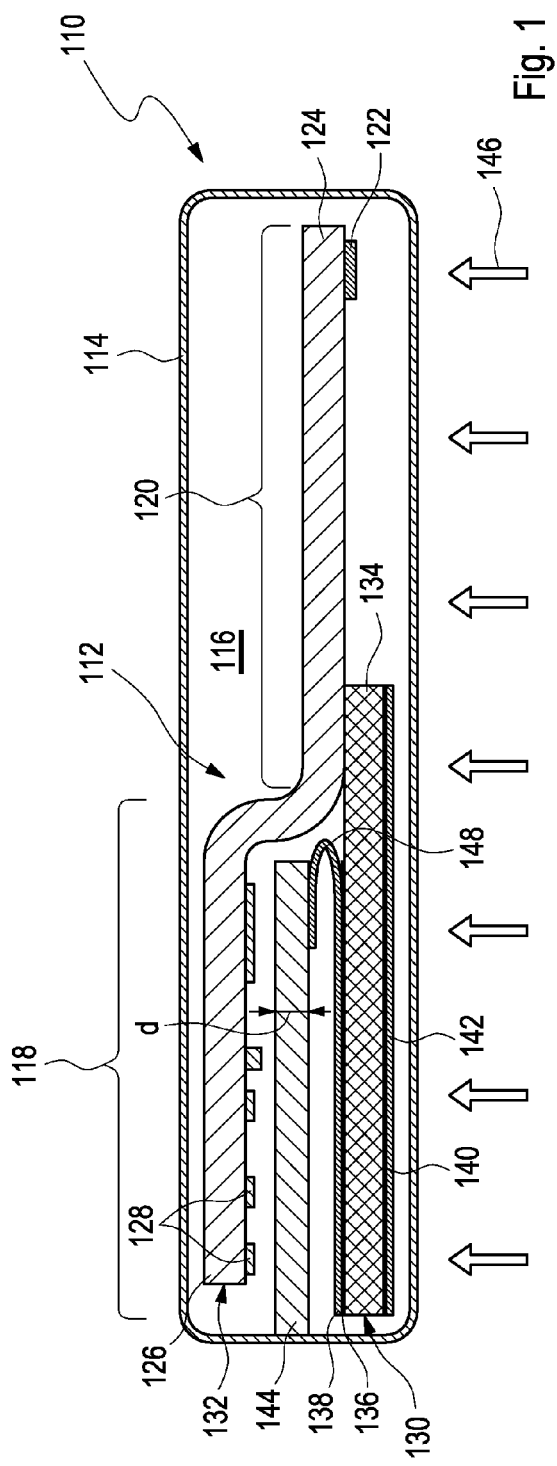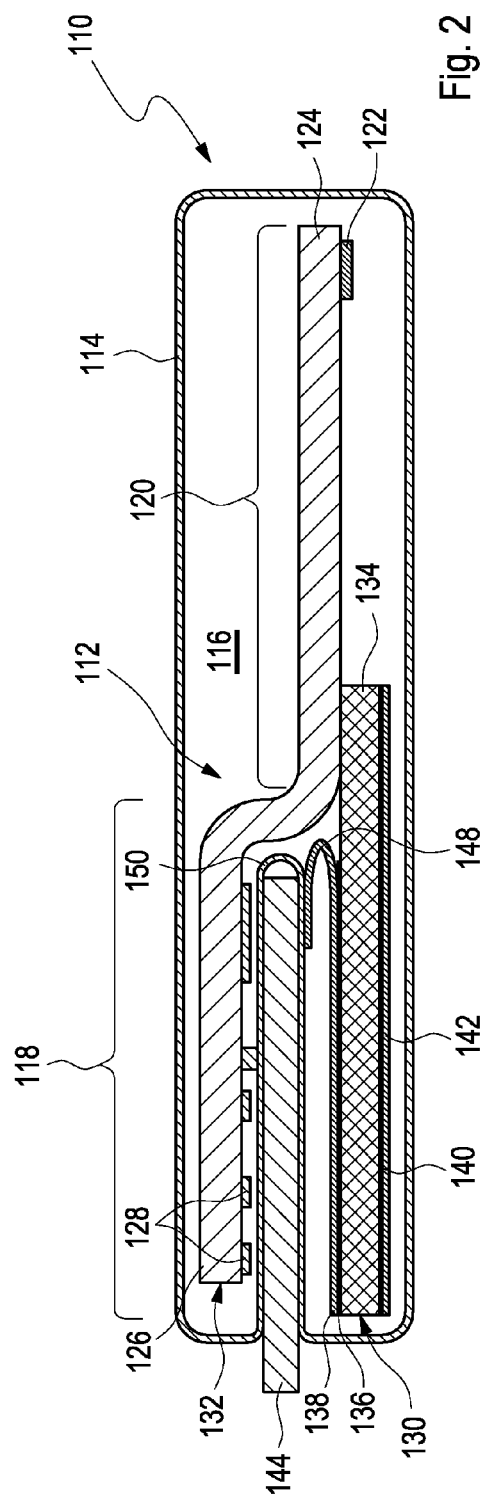

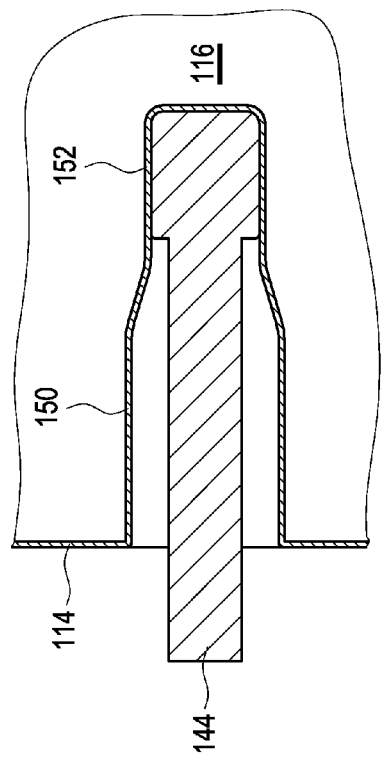
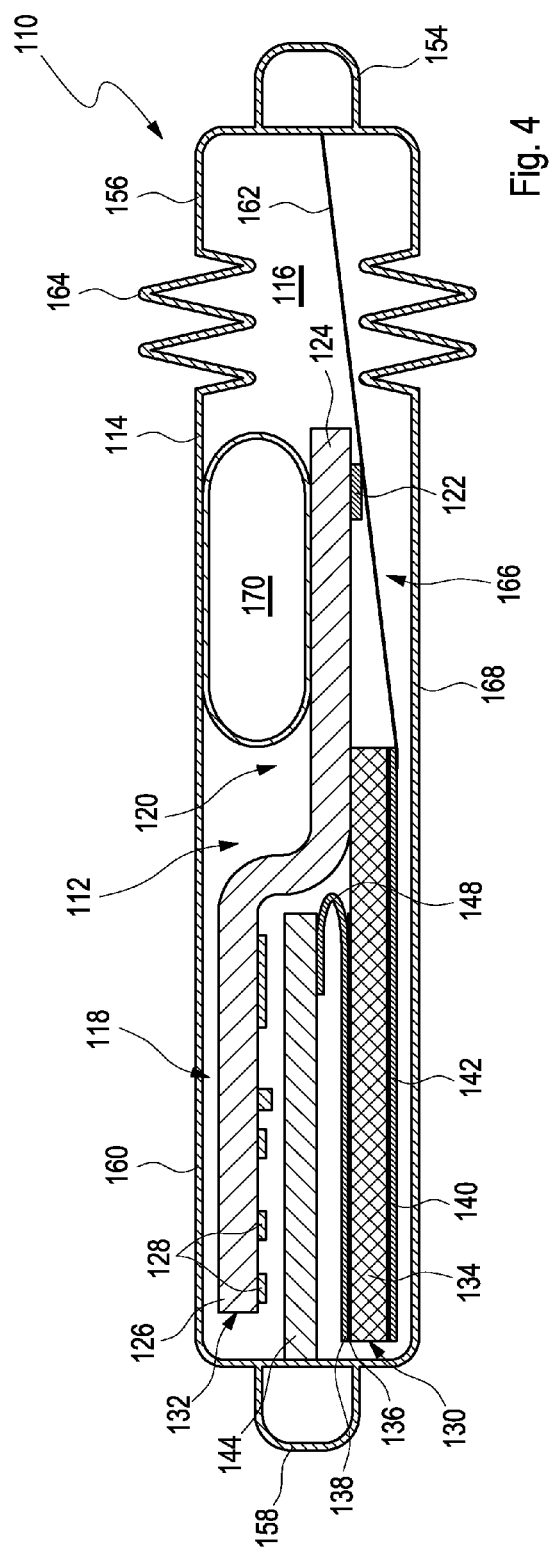

METHOD AND STERILIZING DEVICE FOR STERILIZING AN IMPLANTABLE SENSOR

RELATED APPLICATIONS

This application claims priority to EP11 191 283.8, filed Nov. 30, 2011 which is hereby incorporated by reference in its entirety.

BACKGROUND

The invention relates to a method for sterilizing an implantable sensor and to a sterilizing device for sterilizing an implantable sensor. The sensor serves for sensing at least one analyte in a body tissue. The sensor may particularly be an electrochemical sensor, which is set up for qualitatively and/or quantitatively sensing one or more analytes in a body tissue by electrochemical means. Such sensors are used, for example, in the monitoring of blood glucose concentrations. Other areas of use are also conceivable.

The prior art discloses a large number of sensors which can be completely or partially implanted in a body tissue and which serve for monitoring certain bodily functions, in particular for monitoring one or more concentrations of certain analytes. Without restricting further possible configurations, the invention is described hereinafter with reference to a blood glucose monitoring device. In principle, however, the invention can also be transferred to other types of analytes.

In addition to so-called point measurements, in which a sample of a bodily fluid is taken from a user in a targeted fashion and investigated for the analyte concentration, continuous measurements are also increasingly becoming established. Thus, for example, in the recent past a continuous glucose measurement in the interstitium, which is also referred to as continuous monitoring, CM, has become established as an important method for managing, monitoring and controlling a diabetes status. Directly implantable electrochemical sensors, which are often also referred to as needle-type sensors (NTS), are generally used for this. In this case, the active sensor region is brought directly up to the measuring site, which is generally arranged in the interstitial tissue, and glucose is converted into electrical current, for example using an enzyme, for example glucose oxidase, where the current is in proportion to the glucose concentration and can be used as a measured variable. Examples of such transcutaneous measuring systems are described in U.S. Pat. No. 6,360,888 B1 and in US 2008/0242962 A1.

Present-day continuous monitoring systems are consequently generally transcutaneous systems. This means that the actual sensor part of the sensor with the electrodes is arranged under the user's skin in a body tissue. An electronics part, which is often also referred to as the evaluation and/or control part or else as the patch, is generally located outside the user's body however, that is to say outside the human or animal body. The sensor part is in this case generally applied by means of an insertion aid, which is likewise described by way of example in U.S. Pat. No. 6,360,888 B1. Other types of insertion aids are also known. The time for which a sensor is worn is generally about 1 week.

Complete or partial insertion of the sensor into a body tissue generally requires that completely or partially implantable components of the sensor must be sterilized in accordance with existing standards for use on a human and/or animal. In the case of enzymatically based electrochemical glucose sensors, the enzyme is directly embedded in the electrode or in contact with the interstitium via a protective layer, i.e. the electrodes are exposed. Chemical or thermal sterilization is accordingly generally ruled out, since in the case of such forms of sterilization the enzyme of the electrodes would be damaged. Therefore, generally only radiation sterilization can be used.

Here, however, there is the problem that electronic components of the sensor generally do not withstand direct exposure to radiation, for example to beta radiation or electron radiation, at the radiation doses that are typically necessary (usually 25 kGy). Particular, semiconductor-based active electronic components, such as for example high-impedance amplifier components or potentiostats, are not usually capable of withstanding radiation sterilizations with beta radiation at the radiation doses mentioned without suffering losses in function.

The prior art discloses a large number of methods by means of which protection of sensor elements during radiation sterilization can take place. Thus, for example, a method for producing integrated, diagnostic test elements is described in WO 2006/005503 A1. The test elements have a puncture region and a detection region. The detection region on the test element is shielded from electron radiation that is used for the sterilization. It is also described, inter alia, that the test elements may be arranged in a package, and that the package may be designed such that the detection region of the test elements is shielded from electron radiation and that irradiation of the entire package is performed.

In U.S. Pat. No. 5,496,302 there is described a method for sterilizing a selected region of a product and for producing a sterile product from two or more components that cannot be sterilized in the same way. This involves using a system of tubes with a sterile fluid, in which one part of a housing is sterilized with electron radiation, while another part is protected from the effects of the electron beams by a shielding.

In US 2008/0255440 A1 there is described a sensor package with an implantable sensor. The implantable sensor has an electrode region and an electrical contact region. The sensor is sterilized by beta rays, the package being designed in such a way that the electrical contact region is sterilized, whereas the electrode region remains protected. The package may, for example, protect a sensor part from the influence of further gases that are used for sterilizing electronic components.

In U.S. Pat. No. 6,594,156 B1 there is described a device for protecting electrical circuits during high-energy radiation sterilization. The device comprises a carrier substrate and a protective housing for electronic components. The protective housing is hermetically coupled to the carrier substrate of the electronic components and protects them from the effects of the radiation sterilization. Also described are electronic circuits which are sterilized with a predetermined radiation dose and in which, after the sterilization, the gain factor is not reduced beyond a certain amount and the proportionality between the collector current and the base current is retained.

The solutions known from the prior art have many technical challenges and even disadvantages. Thus, the known solutions are generally not set up for sterilizing a sensor or a sensor system that can be used on a human body without further complex steps. In particular, it is generally not taken into consideration that such a sensor system has parts coming into contact with the skin which on the one hand must be sterile but on the other hand must be in direct contact with the sensitive electronics. In order that the sensor system is sterilized to the entire extent that is necessary, with known devices and methods a number of successive sterilizing methods are often used, such as for example radiation sterilization and chemical sterilization.

Furthermore, the devices known from the prior art are often of such a complex design that they are virtually unusable in industrial processes. Thus, before and after the radiation sterilization, complex preparation or subsequent treatment of the sterilizing device is generally required, during which re-contamination of the sensors may take place. At the same time, however, the sterilizing devices are so complex that they generally could not be delivered to a final customer as a complete unit, together with the shielding device.

SUMMARY

It is therefore desirable to provide a method and a sterilizing device for sterilizing an implantable sensor for sensing at least one analyte in a body tissue which at least largely avoid the disadvantages of the methods and devices described above. In particular, it is desirable to provide a method and a sterilizing device which can be handled in an easy way but nevertheless permit all-round sterilization of the entire sensor and can also be used on an industrial scale for the mass production of sensors.

A method and a sterilizing device for sterilizing an implantable sensor for sensing at least one analyte in a body tissue is disclosed herein. Advantageous features of the method and device, which can be realized individually or in any desired combination, are also disclosed herein.

The method can be carried out here using the sterilizing device disclosed herein. On the other hand, the sterilizing device can be set up for carrying out a method disclosed herein. Accordingly, reference can be made to the description of the sterilizing device for possible details of the method. On the other hand, reference can be made to the features of the method with respect to possible details of the sterilizing device, so that appropriate devices may be used to set up the sterilizing device for carrying out the method and/or for being used in the method. Other designs of the method and/or other designs of the sterilizing device are however also possible in principle.

In a first embodiment, a method for sterilizing an implantable sensor for sensing at least one analyte in a body tissue is proposed. An implantable sensor is generally understood as meaning a sensor which can be completely or partially introduced into a body tissue of a human or animal user. A sensor for sensing at least one analyte in a body tissue is generally understood as meaning a device which is set up for qualitatively or quantitatively detecting the presence of the at least one analyte in the body tissue. The at least one analyte may be, for example, a metabolite and/or another substance which may be present in differing concentrations in a human or animal body tissue, for example in a bodily fluid contained in the body tissue. In particular, the at least one analyte may be an analyte selected from the group comprising blood glucose, lactate and cholesterol. Other analytes are however also detectable in principle.

Sterilization is, in principle, a method in which bacteria are killed off. In particular, these bacteria can be killed off completely so that after the sterilizing method bacterial growth it is no longer possible. As stated below, the sterilization may in particular comprise a radiation sterilization with ionizing radiation, particularly preferably with particle radiation and in particular by means of β radiation and/or electron radiation. The radiation may, for example, comprise electron radiation with an energy of 1.0 MeV to 10 MeV, in particular of 2 MeV to 3 MeV, and particularly preferably of 2.5 MeV.

The sensor has at least one sensor part which can be introduced into the body tissue and has at least one sensor electrode for sensing the analyte and at least one electronics part.

The electronics part has at least one electronic component and is connected to the sensor part. This connection may, in particular, be a mechanical connection or comprise a mechanical connection. Alternatively or preferably, this connection between the electronics part and the sensor part may additionally also comprise at least one electrical connection, for example at least one electrical connection between at least one electronic component of the electronics part and at least one sensor electrode of the sensor part, for example via at least one electrical supply lead. Generally, the electronics part may therefore preferably be connected to the sensor part mechanically and electrically.

The sensor part may be completely or partially implanted in the user's body tissue. For example, the sensor part may be flexibly configured. For example, the sensor part may be completely or partially designed as a sensor strip, with a flexible substrate, which can be received in the body tissue. Other designs are however also possible in principle.

The at least one sensor electrode is set up in such a way that the sensor can sense the at least one analyte by electrochemical means. Thus, the at least one sensor electrode may particularly comprise at least one working electrode and at least one further electrode. The at least one working electrode may, for example, comprise at least one conductive electrode layer, which is coated with at least one enzyme, and possibly one or more additional substances. The at least one enzyme may be, for example, an enzyme which is adapted to the analytes to be detected. For example, the at least one enzyme may comprise glucose oxidase and/or glucose dehydrogenase. Other species of enzymes are however also possible in principle. Furthermore, a coating of the sensor electrode may comprise one or more mediators and/or one or more further auxiliary substances for the electrochemical detection of the at least one analyte. The at least one further electrode may preferably comprise at least one reference electrode and/or at least one counterelectrode. For example, the at least one reference electrode may comprise an Ag/AgCl electrode. The at least one counterelectrode may, for example, comprise a metal electrode, preferably of noble metal, a carbon electrode or an electrode of an electrically conducting polymer. Other designs of the electrodes are however also possible in principle. In particular, the at least one electrode may consequently comprise two, three or more electrodes.

The sensor part is connected to the electronics part. In particular, the sensor part and the electronics part may together form a unit, which preferably cannot be separated without destroying the sensor. For example, the sensor part and the electronics part may share at least one substrate. The connection may also comprise a releasable or unreleasable adhesive connection or clamping connection, which ensures the mechanical and electrical connection between the sensor part and the electronics part.

The sensor part may, for example, have a layered structure. In particular, the sensor part may comprise at least one plastics substrate, for example a polyester substrate or a polyimide substrate. Other designs are also possible.

The electronics part is preferably arranged outside the body tissue during the sensing of the at least one analyte in the body tissue. The electronics part has the at least one electronic component. This at least one electronic component may particularly be connected to the at least one electrode directly or indirectly, via the connection between the sensor part and the electronics part. In particular, the at least one electronic component may comprise at least one active semiconductor component. Particularly preferably, the electronic component may comprise at least one amplifier component, preferably a high-impedance amplifier component with an input resistance of at least 1 GΩ, preferably of at least 100 GΩ. In particular, the at least one electronic component may comprise a potentiostat.

The electronics part may, for example, for its part have at least one substrate, preferably a flexible substrate. The substrate may, for example, comprise a leadframe, to which the at least one component has been applied. The substrate of the electronics part may, for example, be connected to the substrate of the sensor. Furthermore, the electronics part may be connected to the at least one electrode of the sensor part by one or more supply leads.

In one embodiment, the method has the following steps, which are preferably carried out in the sequence mentioned. A different sequence is also possible in principle. Furthermore, one or more method steps may also be carried out in parallel or overlapping in time. Furthermore, one or more of the method steps described hereinafter may be carried out repeatedly. Furthermore, the method may have one or more additional steps that are not mentioned.

In one method step (method step a)), the sensor is introduced into at least one package. Introduction is understood here generally as meaning providing the at least one sensor for the method in the package. The sensor may in this case be in a finished state or else, as described in more detail hereinafter, in a semifinished state, where one or more subsequent method steps may still be required to bring the semifinished sensor into a finished state that can be used on the user. Both options are comprised within the scope of the concept of introducing the sensor into the package.

A package is understood generally within the context of the present disclosure as meaning a device which encloses, preferably completely encloses, the sensor and closes off the sensor from environmental influences. Thus, the package closes off the sensor from the surroundings such that it is sealed from bacteria, so that no bacteria can get to the sensor through the package. The package should in this case generally not be regarded as a component part of the sensor and is generally designed in such a way that, for using the sensor, it is separated from the sensor. Thus, the sensor may particularly be movably accommodated in the package. In particular, the package may preferably not be connected to the sensor. The package may, for example, be completely or partially produced from a plastics material and/or completely or partially produced from a metallic material. Particularly preferably, the package comprises at least one sheeting, preferably at least one plastics sheeting. For example, the plastics sheeting may comprise at least one of the following plastics: PE, PP, PC, PET and PETG. Other plastics can however also be alternatively or additionally used in principle. Furthermore, metallic sheetings and/or sheetings of composite materials can also be alternatively or additionally used. The package may particularly be of a deformable design, in particular a flexible design. Alternatively or additionally, the package may however also be of a completely or partially rigid design. As an alternative or in addition to a sheeting, the package may furthermore also comprise at least one moulded part, for example at least one plastics moulded part. For example, moulded parts which can be produced by an injection-moulding process, injection-blow-moulding process or similar shaping processes may be used.

The package also accommodates a radiation shield, shielding the electronics part. A radiation shield should be understood here as meaning a device which attenuates the radiation that is used for the sterilization by at least a factor of 10, preferably by at least a factor of 100. Radiation shield designs are described in the literature as can be found for example in: W. Demtröder: Experimentalphysik [Experimental physics], volume 4: Kern-, Teilchen- and Astrophysik [Nuclear, particle and astrophysics], Springer Verlag, Heidelberg 1998, pp. 91-92. For example, the radiation shield may have a plate-like element and/or a moulded part which, when exposed to directed sterilizing radiation, must first be passed by the sterilizing radiation before it reaches the electronics part. The electronics part can in this case be completely or partially shielded by the radiation shield, at least the electronic component and/or at least one of the electronic components, preferably the semiconductor component, and particularly preferably the at least one high-impedance amplifier, and/or the at least one potentiostat, being shielded by the radiation shield.

The feature that the package accommodates the radiation shield may be understood here on the one hand as meaning that the radiation shield is a component part of the package. On the other hand, however, as set out in more detail below, the radiation shield may be accommodated loosely in and/or on the package and, for example, be designed such that it can be separated from the package. In particular, the package may completely or partially encapsulate the radiation shield. For example, the radiation shield may be accommodated in an interior space of the package. As an alternative or in addition, however, the radiation shield may also be completely or partially arranged outside an interior space of the package, so that at least one wall of the package is arranged between the interior space and the radiation shield. For example, the radiation shield may be completely or partially arranged in one or more pockets of the package that protrude into the interior space, so that the radiation shield protrudes into the interior space of the package, although at least one wall of the package is preferably arranged between the interior space and the radiation shield. Various designs are possible and are described in more detail below by way of example. All of the options, that is to say options in which the radiation shield is arranged within the package or merely on the package, are intended to be comprised by the feature that the package accommodates the radiation shield.

The package and the radiation shield preferably form a unit, irrespective of whether this unit is separable or not.

In a further method step (method step b)), which is preferably carried out completely after method step a), the sensor is irradiated in the package with sterilizing radiation from at least one irradiating direction. For example, the sensor may be irradiated with the sterilizing radiation from one irradiating direction and/or from two irradiating directions. This irradiation may preferably be performed completely, so that the entire sensor is irradiated by the sterilizing radiation, with the exception of those portions which are shielded by the radiation shield. Punctiform irradiation is however also possible in principle. However, the irradiation is preferably performed over a large area such that initially all of the component parts of the sensor are irradiated, though, as described above, the radiation shield shields one or more regions of the sensor from the sterilizing radiation.

A sterilizing radiation should be understood as meaning generally an ionizing radiation, which has bactericidal effects. This may in principle be electromagnetic radiation and/or particle radiation. However, as stated above, the use of particle radiation, in particular βradiation and/or electron radiation, is particularly preferred. For example, during the radiation sterilization with the sterilizing radiation, the sensor may be exposed to a dose of at least 5 kGy, particularly preferably of at least 10 kGy, and in particular of at least 20 kGy, or even at least 25 kGy. One or more radiation sources may be used, for example, for the radiation sterilization, for example radioactive βemitters and/or electron radiation sources. In the radiation sterilization, that is to say the irradiation of the sensor with the sterilizing radiation, which is preferably performed by being directed from at least one spatial direction, preferably at least two spatial directions, the radiation shield shields the electronic component of the electronics part from the sterilizing radiation. If a number of electronic components are contained, the radiation shield may in particular shield at least one of these electronic components, for example at least one semiconductor component, preferably an active semiconductor component, in particular at least one amplifier, preferably at least one high-impedance amplifier, and particularly preferably a potentiostat. Furthermore, the radiation shield is arranged in such a way that the sensor part is sterilized by the sterilizing radiation. By contrast with the prior art described above, in which the sensor part is generally shielded, it is therefore proposed in the present case to completely or partially shield the electronics part, but to sterilize the sensor part to be implanted, which is introduced directly into the body tissue. The radiation damage that possibly occurs thereby to the at least one sensor electrode, for example to the sensor chemistry of the sensor electrodes, for example the at least one enzyme, is generally negligible or can be compensated by appropriate calibration after the radiation sterilization. At the same time, however, sensitive semiconductor components, such as for example potentiostats, can be shielded from the sterilizing radiation, so that the radiation sterilization does not generally entail any losses in function for these components. In this way, sensors in which an electronics part is specifically completely or partially protected from radiation damage can be produced in particular in one piece or in the form of a unit. During and after the radiation sterilization, the sensor can remain in the package, which is preferably completely closed during the radiation sterilization and can, for example, prevent re-contamination of the sensor after the radiation sterilization. The sensor can be delivered to a final customer in the package, the final customer opening the package, for example, in order to completely or partially implant the sensor. For example, for this opening, the package may have at least one predetermined breaking point, for example a weakening of a wall thickness, along which tearing open of the package is possible. An opening with a stopper or a screw closure may also be provided.

As stated above, in method step a), the sensor may be provided within the package. As likewise stated, the sensor may in this case be provided as a finished sensor or else as a semifinished product, that is to say as an intermediate product. In the latter case, one or more method steps may be required in order to complete final assembly of the sensor. Particularly preferably, the method is carried out in such a way that this final assembly is performed within the package, without the package being opened. This final assembly may particularly be performed after the radiation sterilization of method step b). After introducing the sensor into the package, the package may preferably be closed, in particular such that it is sealed from bacteria, for example by at least one closure element and/or by interlocking engagement, for example welding. For example, a sheeting of the package and/or a sheeting part of the package may be welded.

Thus, after carrying out method step a), the sensor may in particular have at least a first part and at least a second part. The first part may be sterilized in method step b). On the other hand, in method step b), the second part may be shielded from the sterilizing radiation completely or partially, i.e. completely or for example in certain regions, by the radiation shield. After carrying out method step b), that is to say after carrying out the radiation sterilization, the first part and the second part may be connected within the package, in particular without opening the package.

This means that the package is preferably designed in such a way that external intervention by a user is possible in such a way that the first part and the second part can be connected to each other within the package after the radiation sterilization. For this purpose, the package may, for example, be of a deformable design in such a way that the described final assembly, in which the first part and the second part are connected to each other within the package, is possible.

Thus, the package may be generally deformable in such a way that, when there is a deformation of the package after carrying out method step b), the first part and the second part are moved in relation to each other in such a way that they are connected to each other. In particular, the first part and the second part may be pressed against each other. As set out in more detail below, this can be accomplished by the first part and the second part being guided through at least one constriction during the movement that is triggered by the deformation by the package, the first part and the second part being pressed against each other by the constriction. This design is described hereinafter in particular by reference to a layered structure of the sensor, one or more layers of the sensor being sterilized as a first part, one or more further layers of the sensor being shielded completely or partially, i.e. as a whole or in at least one region, from the sterilizing radiation during the radiation sterilization as a second part. Apart from a layered structure, other designs of the final assembly within the package are however also possible in principle.

In a preferred design of the method, the electronics part is designed in such a way that it has a layered structure as a whole or in at least one region. A layered structure should be understood as meaning generally a structure in which one or more layers are applied one on top of the other. At least one of these layers may, for example, have at least one leadframe, to which the at least one electronic component of the electronics part has been applied and/or into which the at least one electronic component of the electronics part has been introduced. The layered structure has at least one overlayer. In method step b), the overlayer is in this case arranged in such a way in relation to the radiation shield that the overlayer is at least partially sterilized by the sterilizing radiation. An overlayer should be understood in this case as meaning a layer which in the said layered structure covers over at least one further layer and/or at least one further component, for example the electronic component. For example, in the case of a finally assembled sensor, the overlayer may represent a layer which forms a surface of the sensor and which can, for example, come into contact with a skin and/or a bodily fluid and/or the body tissue of a user.

The overlayer may particularly comprise an adhesive layer, in particular at least one adhesive layer for fixing the implantable sensor on a surface of the skin. Thus, the implantable sensor may in particular be designed in such a way that the sensor part protrudes into the body tissue through at least one insertion opening, whereas the electronics part is arranged completely or partially outside the body tissue, for example on a surface of the skin of a user. The electronics part may be fixable on the surface of the skin of the user by the said at least one adhesive layer, for example a plaster.

The method may also be designed in such a way that, as described above, the radiation sterilization is followed by the final assembly, in which the overlayer is applied to one or more further layers. In particular, after carrying out method step b), the overlayer, which by then is sterilized, can be applied to the electronic component within the package. This application may be performed directly or indirectly, that is to say in such a way that the overlayer directly contacts the at least one electronic component directly, or indirectly by one or more intermediate layers being applied between the overlayer and the electronic component, for example one or more further layers and/or one or more encapsulations. Various designs are possible. In any event, the application may be performed in such a way that the at least one overlayer is arranged between the electronic component and an outer surface of the sensor. The application of the overlayer to the electronic component may in particular be performed in such a way that, during this application, the package is not opened. During the final assembly, the sensor may therefore still be completely protected from re-contamination by the package.

After applying the overlayer, the overlayer may in particular, as stated above, form an outer surface of the sensor, in particular of the electronics part of the sensor. This may in particular be designed in such a way that the outer surface of the electronics part, particularly preferably the entire surface of the implantable sensor, is sterilized all around. In other words, the method may be carried out in such a way that the surface of the sensor is completely radiation-sterilized, even in the region of the electronics part, while the at least one electronic component may nevertheless be protected from radiation damage by use of the radiation shield and subsequent final assembly within the package.

As stated above, the package may in particular be of a completely or partially deformable design. The final assembly, in which the first part and the second part are connected to each other, in particular by the overlayer being applied to the electronic component, may be accomplished by a deformation. Thus, the package may in particular be of a deformable design in such a way that, when there is a deformation of the package, the sensor is moved through at least one constriction, in particular is pulled, the overlayer being pressed onto the electronic component by the constriction. This constriction may be designed in various ways and may, for example, comprise at least one gap. This gap is preferably not rigidly formed, in order to avoid damage to the sensor. In this way, for example, a laminating process may be performed, the overlayer being laminated onto the at least one electronic component. For example, the constriction may be formed in the package by at least one pressure pad, which interacts with a counter element, for example a rigid counter element, and/or a further pressure pad, it being possible for a gap to form between the pressure pad and the counter element.

The deformation of the package may be performed in particular by using a flexible package material, which is stretchable and/or deformable. As an alternative or in addition, the package may also, for example, have specifically deformable elements, such as for example at least one bellows.

As stated above, the radiation shield may be a component part of the package or may however merely be connected to the package and/or be accommodated in the package and/or on the package, so that the radiation shield itself does not form a component part of the actual package. In the latter case, the radiation shield may be separated from the package, in particular after carrying out method step b), in order for example to be used for the sterilization of further sensors. Thus, the radiation shield may, in particular, be designed as a reusable radiation shield.

This separation of the radiation shield from the package may in particular comprise removal of the radiation shield from a complete or partial encapsulation of the radiation shield by the package. The separation may in particular be performed at the same time as or at least overlapping in time or in one operation with the deformation of the package that is described above. Thus, during the deformation of the package, the radiation shield may at the same time be separated from the package, in particular be completely or partially removed from a complete or partial encapsulation by the package. For example, before the deforming of the package, the radiation shield may have been inserted from the outside into at least one finger of the package protruding into an interior space of the package. For example, the package may generally form an interior space in which the sensor is accommodated and stored such that it is sealed from bacteria during the radiation sterilization and preferably during the final assembly. A finger should be understood as meaning generally a projection of an inner wall of the package that protrudes into the interior space. For example, the finger may form or comprise at least one pocket protruding into the interior space. This finger may be of a tubular design and/or be designed in some other way such that the radiation shield likewise protrudes into the interior space and can shield the at least one electronic component of the electronics part during the radiation sterilization. The radiation shield may therefore generally be arranged in such a way that it is not accommodated in the interior space, so that, for example, the radiation shield itself does not have to be sterile and, for example, can be reused without sterilization of the radiation shield being required.

The method may be carried out in particular in such a way that the finger of the package which protrudes into the package during the radiation sterilization, in particular into the interior space of the package, is pulled out from an interior space of the package during the removal of the radiation shield. This may be performed, for example, in the same way as the finger of a glove can be turned inside out when the hand is pulled out. Examples are described in more detail below.

The package may, in particular, be of a deformable design in such a way that the sensor is connected to a first package part of the package, for example by a releasable connection, the radiation shield being movable with a second package part of the package, the first package part and the second package part being connected to each other during the deformation of the package in such a way that a bacteria-sealed shielding of the sensor continues to be ensured, for example until the package is opened by a user for the purpose of removing the sensor from the package.

During the deformation of the package, the overlayer may be applied over a large area from at least one side to a substrate of the electronics part that is carrying the electronic component, in particular is adhesively attached and/or laminated on. However, as described above, other types of final assembly are also possible in principle.

The package may also have at least one grip, preferably at least two grips, for the package to be held by a user carrying out the deformation. For example, at least a first grip may be connected to a first package part, described above, and at least a second grip may be connected to at least a second package part.

The radiation shield may, in particular, comprise at least one metallic radiation shield. The metallic radiation shield may, in particular, have a thickness of 1 mm to 10 mm, preferably a thickness of 3 mm to 7 mm, and particularly preferably a thickness of 5 mm. Other designs are, however, also possible in principle. The metallic radiation shield may, in particular, be completely or partially produced from at least one metallic material, selected from the group comprising: aluminium, iron, steel, lead and copper. As an alternative or in addition, however, the use of other metals is also possible. The said metals and/or other metals may be in a pure form and/or in the form of alloys.

In addition to the sensor, at least one further element may also be accommodated in the package and preferably be sterilized at the same time during the radiation sterilization. Thus, for example, in method step a), at least one medical aid may additionally be introduced into the package, i.e. be provided in the package. A medical aid should be understood as meaning generally a device which can be used in the course of a medical process, that is to say in the course of a diagnostic and/or surgical and/or therapeutic process. In particular, the medical aid may be a disposable aid. For example, the medical aid may be a device which can come into contact with a bodily fluid and/or an open body tissue of a user. In particular, the medical aid may comprise at least one insertion aid. An insertion aid should be understood, for example, as meaning an element which is set up for introducing at least the sensor part of the sensor into the body tissue. For example, the insertion aid may comprise at least one cannula. With respect to possible designs of the implantable sensor and with respect to possible designs of the insertion aid, reference can be made in principle to the above description of the prior art. Other designs are however also possible in principle.

In a further embodiment, a sterilizing device for sterilizing an implantable sensor for sensing at least one analyte in a body tissue is disclosed. A sterilizing device should be understood here as meaning generally a device which can accommodate the sensor during and preferably also after the radiation sterilization. The sterilizing device may, for example, be reversibly inserted as a whole into a sterilizing apparatus, which for example has a radiation source for generating the sterilizing radiation, for example a βradiation source and/or an electron radiation source. The sterilizing device may, for example, form a unit which can be handled as a whole and which can, for example, be completely or partially delivered later to a final customer or user.

The sterilizing device serves in particular for use in a method according to one or more of the designs described above and/or according to one or more of the exemplary embodiments described in more detail hereinafter.

The sterilizing device comprises at least one implantable sensor for sensing at least one analyte in a body tissue. The sensor has at least one sensor part which can be introduced into the body tissue and has at least one sensor electrode for sensing the analyte and at least one electronics part. The electronics part has at least one electronic component and is connected to the sensor part. Further possible designs of the sensor are also feasible.

The sterilizing device also comprises at least one package. The package closes off the sensor such that it is sealed from bacteria. The package accommodates at least one radiation shield that shields the electronic component of the electronics part during radiation sterilization. As described above, the radiation shield may be a component part of the package or else be releasably accommodated in the package, i.e. connected to the package in such a way that the radiation shield can be separated from the package after the radiation sterilization. Further possible designs are also feasible.

The radiation sterilization may, in particular, be set up in such a way that it can be used during a method disclosed herein.

Thus, the sensor may, in particular, have at least a first part and at least a second part, the first part being sterilizable in the package during the radiation sterilization, the second part being shielded by the radiation shield during the radiation sterilization, the first part and the second part being able to be connected within the package after carrying out the radiation sterilization, in particular without opening the package. The sterilizing device may therefore be set up in such a way that a final assembly of the sensor can be carried out within the package after the radiation sterilization.

In particular, as discussed above, the package may be of a deformable design. During the deformation of the package after carrying out the radiation sterilization, the first part and the second part may be movable in relation to each other in such a way that they can be connected to each other. In particular, the first part and the second part may be pressed against each other.

As discussed above, the electronics part may in particular have at least one layered structure. The layered structure may, in particular, have at least one overlayer, it being possible for the package to be designed in such a way that, during the radiation sterilization, the overlayer is arranged in relation to the radiation shield in such a way that the overlayer can be at least partially sterilized by the sterilizing radiation, while the electronic component is shielded. The package may be designed in such a way that, after carrying out the radiation sterilization, the overlayer can be applied to the electronic component, in particular pressed on and/or laminated on, within the package, in particular without opening the package. As discussed above, the package may, in particular, be of a deformable design in such a way that, during a deformation of the package, the sensor is moved through at least one constriction, in particular pulled, it being possible for the overlayer to be pressed onto the electronic component by the constriction. The constriction may, in particular, be formed in the package by at least one pressure pad.

The package may be designed, in particular, in such a way that, during the deformation, at the same time the radiation shield can be separated from the package, in particular completely or partially from a complete or partial encapsulation by the package. Thus, for example, before the deforming of the package, the radiation shield may have been inserted from the outside into at least one finger of the package protruding into an interior space of the package. During the removal of the radiation shield, the finger of the package may preferably be pulled out from the interior space of the package. Further possible designs are also feasible.

The package may, in particular, be of a deformable design in such a way that the sensor is connected to a first package part of the package, the radiation shield being movable with a second package part of the package, the first package part and the second package part remaining connected to each other during the deformation of the package in such a way that a bacteria-sealed shielding of the sensor is ensured during the deformation.

As described above, the package may, in particular, have at least one bellows. For example, the first package part and the second package part may be connected to each other by the bellows. The package may also have at least two grips, for example a first grip, connected to the first package part, and a second grip, connected to the second package part. The provision of these grips may facilitate deforming of the package.

As described above, the package may also have, in particular, at least one sheeting, preferably at least one plastics sheeting and/or at least one metal sheeting and/or at least one laminate sheeting. The sheeting may be attached in particular in a region of the package which is radiated through by the sterilizing radiation during the sterilization. For example, the sheeting may have a thickness of at most 1 mm, preferably of at most 500 μm, and particularly preferably a thickness of 10 μm to 100 μm. In particular, the package may have one or more of the plastics described above.

Before or after a sterilization, the package may be checked for gas impermeability and/or sterile sealing by pressure or vacuum methods that are known in the art.

As also discussed above, the package may, in particular, have at least one predetermined breaking point for the irreversible opening and removal of the sensor, for example by a final customer and/or user. Thus, for example, method steps a) and b), and possibly a final assembly of the sensor, may be performed within the package by a manufacturer. The sensor can subsequently be stored and delivered, for example to an intermediate dealer and/or a final customer, with the final customer being able, for example, to remove the sensor after opening the package, for inserting the sensor into the body tissue. The opening is performed, for example, by tearing open a predetermined breaking point, by removing a stopper or removing a screw closure. The predetermined breaking point may, for example, comprise at least one weakening in the package, for example a material weakening in the form of a linear weakening, along which the package can be torn open and opened. Other designs are, however, also possible in principle. The method and the sterilizing device according to one or more of the designs described above have numerous advantages over known methods and devices. In particular, now a sensor with an electronics part and a sensor part, which may also be formed in one piece, can be sterilized without any problem. In particular, for example, commercially available potentiostats can be used. For example, radiation sterilization with 25 kGy can be withstood without functional losses.

While the devices and methods that are known from the prior art are not set up for sterilizing a sensor system which can be used on a human and/or animal body without further complicated steps, this is possible without any problem according to the present invention. In particular, a sensor may now have parts coming into contact with the skin and/or the body tissue and/or a bodily fluid which on the one hand must be sterile but on the other hand are in direct contact with the sensitive electronics. The sensor system of the sensor can now be sterilized to the entire extent that is necessary, for example without having to work with different sterilizing methods. Thus, for example, according to the invention a radiation sterilization can be exclusively used, without for example an additional chemical sterilization being required.

Furthermore, additional working steps in production and additional handling steps in the application can be saved. Thus, a sensor unit which is finally assembled in a completely sterile state can be produced, without subsequently requiring further steps on the part of a user, with the exception of the always required insertion into the body tissue.

The implantable sensor part, which can be implanted subcutaneously, is connected to the electronics part. The electronics part may act completely or partially as an activating or evaluating part of the sensor. Thus, the electronics part may be set up, for example, for carrying out a signal processing and/or a preprocessing of signals. The electronics part may also be set up as a communications part and may, for example, comprise one or more interfaces of the sensor, by means of which the sensor can, for example, pass on measurement data to a user and/or to one or more further devices. Furthermore, the electronics part may also comprise at least one energy supply, that is to say, for example, an independent energy supply and/or an energy store and/or at least one connection by which the energy supply can take place. The implantable sensor part and all other parts coming into contact with the skin can be sterilized by βradiation. The electronics may be completely or partially protected by the radiation shield, preferably a metallic shielding. The radiation shield may optionally be removed from the package, it preferably being possible during this step for a final assembly to be performed, for example a connection between the previously shielded part and a fixing device for fixing the part on the human skin. Thus, the aforementioned first part, which is sterilized in method step b), may comprise such a fixing device for fixing the sensor on the human skin, for example at least one adhesive layer.

In spite of the necessary sterilization, for example with high-energy beams, commercially available electronics can generally be used in the electronics part of the sensor. Thus, for example, commercially available electronic components, in particular in the form of semiconductor components, can be used without radiation damage having to be feared.

It should be noted as a further advantage that the option of removing the radiation shield allows the sensor system to have a low profile when it is applied to the patient. Thus, by removing the radiation shield, the package with the sensor accommodated in it can be made extremely small in volume, so that the unit comprising the package and the sensor can be delivered to a final customer. Thus, the costs and the weight of the radiation shield can be saved. It is also advantageous that various components, such as for example a sensor tip, a slit cannula and an adhesive film coming into contact with the skin can be sterilized together in a sterile-sealed package, which may serve as an outer package. After the sterilization, these components can be assembled without opening the package, acting as a sterile package, and/or can be brought into a new relative position with respect to one another.

To sum up, the following, partial list, of embodiments are particularly preferred:

Embodiment 1

A method for sterilizing an implantable sensor for sensing at least one analyte in a body tissue, wherein the implantable sensor has at least one sensor part which can be introduced into the body tissue and has at least one sensor electrode for sensing the analyte and at least one electronics part, the electronics part having at least one electronic component and being connected to the sensor part, the method having the following steps:

a) the implantable sensor is introduced into at least one package, the package closing off the implantable sensor such that it is sealed from bacteria and the package accommodating a radiation shield that shields the electronics part, b) the implantable sensor is irradiated in the package with sterilizing radiation from at least one irradiating direction, in particular with electron radiation, the radiation shield shielding the electronic component of the electronics part from the sterilizing radiation, the radiation shield being arranged in such a way that the sensor part is sterilized by the sterilizing radiation.

Embodiment 2

The method according to the preceding embodiment, wherein, after carrying out method step a), the implantable sensor has at least a first part and at least a second part, the first part being sterilized in method step b), the second part being shielded from the sterilizing radiation by the radiation shield in method step b), wherein, after carrying out method step b), the first part and the second part are connected within the package, in particular without opening the package.

Embodiment 3

The method according to the preceding embodiment, the package being of a deformable design in such a way that, when there is a deformation of the package after carrying out method step b), the first part and the second part are moved in relation to each other in such a way that they are connected to each other, in particular in that the first part and the second part are pressed against each other.

Embodiment 4

The method according to one of the preceding embodiments, the electronics part having a layered structure, the layered structure having at least one overlayer, wherein, in method step b), the overlayer is arranged in such a way in relation to the radiation shield that the overlayer is completely or partially sterilized by the sterilizing radiation.

Embodiment 5

The method of the preceding embodiment, the overlayer comprising an adhesive layer, in particular an adhesive layer for fixing the implantable sensor on a surface of the skin.

Embodiment 6

The method according to one of the two preceding embodiments, wherein, after carrying out method step b), the overlayer is applied to the electronic component within the package, in particular without opening the package.

Embodiment 7

The method according to the preceding embodiment, wherein, after applying the overlayer, the overlayer forms an outer surface of the electronics part.

Embodiment 8

The method according to one of the two preceding embodiments, the package being of a deformable design in such a way that, when there is a deformation of the package, the implantable sensor is moved through at least one constriction, in particular is pulled, the overlayer being pressed onto the electronic component by the constriction.

Embodiment 9

The method according to the preceding embodiment, the constriction being formed in the package by at least one pressure pad.

Embodiment 10

The method according to one of the two preceding embodiments, the package comprising a bellows.

Embodiment 11

The method according to one of the three preceding embodiments, wherein, during the deformation of the package, the radiation shield is separated from the package.

Embodiment 12

The method according to the preceding embodiment, wherein, before the deforming of the package, the radiation shield has been inserted from the outside into at least one finger of the package protruding into an interior space of the package, in particular from the outside.

Embodiment 13

The method according to the preceding embodiment, wherein the finger of the package is pulled out from an interior space of the package during the removal of the radiation shield.

Embodiment 14

The method according to one of the six preceding embodiments, the package being of a deformable design in such a way that the sensor is connected to a first package part of the package, the radiation shield being movable with a second package part of the package, the first package part and the second package part remaining connected to each other during the deformation of the package in such a way that a bacteria-sealed shielding of the sensor is ensured.

Embodiment 15

The method according to one of the seven preceding embodiments, wherein, during the deformation of the package, the overlayer is applied over a large area from at least one side to a substrate of the electronics part that is carrying the electronic component, in particular is adhesively attached and/or laminated on.

Embodiment 16

The method according to one of the eight preceding embodiments, the package having at least one grip, preferably at least two grips, for the package to be held by a user carrying out the deformation.

Embodiment 17

The method according to one of the preceding embodiments, the radiation shield comprising at least one metallic radiation shield.

Embodiment 18

The method according to the preceding embodiment, the metallic radiation shield having a thickness of 1 mm to 10 mm, preferably of 3 mm to 7 mm, and particularly preferably of 5 mm.

Embodiment 19

The method according to one of the two preceding embodiments, the metallic radiation shield comprising at least one metallic metal, selected from the group comprising: aluminium, iron, steel, lead and copper.

Embodiment 20

The method according to one of the preceding embodiments, wherein, in method step a), at least one medical aid, in particular at least one insertion aid, is additionally introduced into the package.

Embodiment 21

A sterilizing device for sterilizing an implantable sensor for sensing at least one analyte in a body tissue, in particular for use in a method according to one of the preceding embodiments, the sterilizing device comprising:

at least one implantable sensor for sensing at least one analyte in a body tissue, wherein the implantable sensor has at least one sensor part which can be introduced into the body tissue and has at least one sensor electrode for sensing the analyte and at least one electronics part, the electronics part having at least one electronic component and being connected to the sensor part;

at least one package, the package closing off the implantable sensor such that it is sealed from bacteria and the package accommodating at least one radiation shield that shields the electronic component of the electronics part during a radiation sterilization.

Embodiment 22

The sterilizing device according to the preceding embodiment, the sterilizing device being set up for being used in a method according to one or more of embodiments 1-19.

Embodiment 23

The sterilizing device according to one of the two preceding embodiments, the sensor having at least a first part and at least a second part, the first part being sterilizable in the package during the radiation sterilization, the second part being shielded by the radiation shield during the radiation sterilization, the first part and the second part being able to be connected within the package after carrying out the radiation sterilization, in particular without opening the package.

Embodiment 24

The sterilizing device according to the preceding embodiment, the package being of a deformable design in such a way that, when there is a deformation of the package after carrying out the radiation sterilization, the first part and the second part are moved in relation to each other in such a way that they are connected to each other, in particular in that the first part and the second part are pressed against each other.

Embodiment 25

The sterilizing device according to one of the preceding embodiments concerning a sterilizing device, the electronics part having a layered structure, the layered structure having at least one overlayer, wherein the package is designed in such a way that, during the radiation sterilization, the overlayer is arranged in such a way in relation to the radiation shield that the overlayer can be at least partially sterilized by the sterilizing radiation, while the electronic component is shielded.

Embodiment 26

The sterilizing device according to the preceding embodiment, the package being designed in such a way that, after carrying out the radiation sterilization, the overlayer can be applied to the electronic component within the package, in particular without opening the package.

Embodiment 27

The sterilizing device according to the preceding embodiment, the package being of a deformable design in such a way that, when there is a deformation of the package, the implantable sensor is moved through at least one constriction, in particular is pulled, the overlayer being pressed onto the electronic component by the constriction.

Embodiment 28

The sterilizing device according to the preceding embodiment, the constriction being formed in the package by at least one pressure pad.

Embodiment 29

The sterilizing device according to one of the two preceding embodiments, wherein, during the deformation of the package, the radiation shield can be separated from the package.

Embodiment 30

The sterilizing device according to one of the three preceding embodiments, wherein, before the deforming of the package, the radiation shield has been inserted from the outside into at least one finger of the package protruding into an interior space of the package.

Embodiment 31

The sterilizing device according to the preceding embodiment, wherein the finger of the package is pulled out from the interior space of the package during the removal of the radiation shield.

Embodiment 32

The sterilizing device according to one of the five preceding embodiments, the package being of a deformable design in such a way that the sensor is connected to a first package part of the package, the radiation shield being movable with a second package part of the package, the first package part and the second package part remaining connected to each other during the deformation of the package in such a way that a bacteria-sealed shielding of the implantable sensor is ensured.

Embodiment 33

The sterilizing device according to one of the preceding embodiments concerning a sterilizing device, the package having a bellows.

Embodiment 34

The sterilizing device according to one of the preceding embodiments concerning a sterilizing device, the package having at least two grips.

Embodiment 35

The sterilizing device according to one of the preceding embodiments concerning a sterilizing device, the package having a plastics sheeting.

Embodiment 36

The sterilizing device according to one of the preceding embodiments concerning a sterilizing device, the package having a predetermined breaking point for irreversible opening and removal of the implantable sensor.

BRIEF DESCRIPTION OF THE DRAWINGS

Further details and features of the invention emerge from the following description of preferred exemplary embodiments. The respective features may be realized on their own or together in combination with one another. The invention is not restricted to the exemplary embodiments. The exemplary embodiments are schematically represented in the figures. The same reference numerals in the individual figures thereby designate elements that are the same or functionally the same or correspond to one another with regard to their functions.

FIG. 1 shows a first exemplary embodiment of a sterilizing device and of a method; and FIG. 2 shows a second exemplary embodiment of a sterilizing device and of a method;

FIG. 3 shows a detailed representation of a means for accommodating a radiation shield in a package;

FIG. 4 shows a third exemplary embodiment of a sterilizing device;

DETAILED DESCRIPTION

Figure 5:
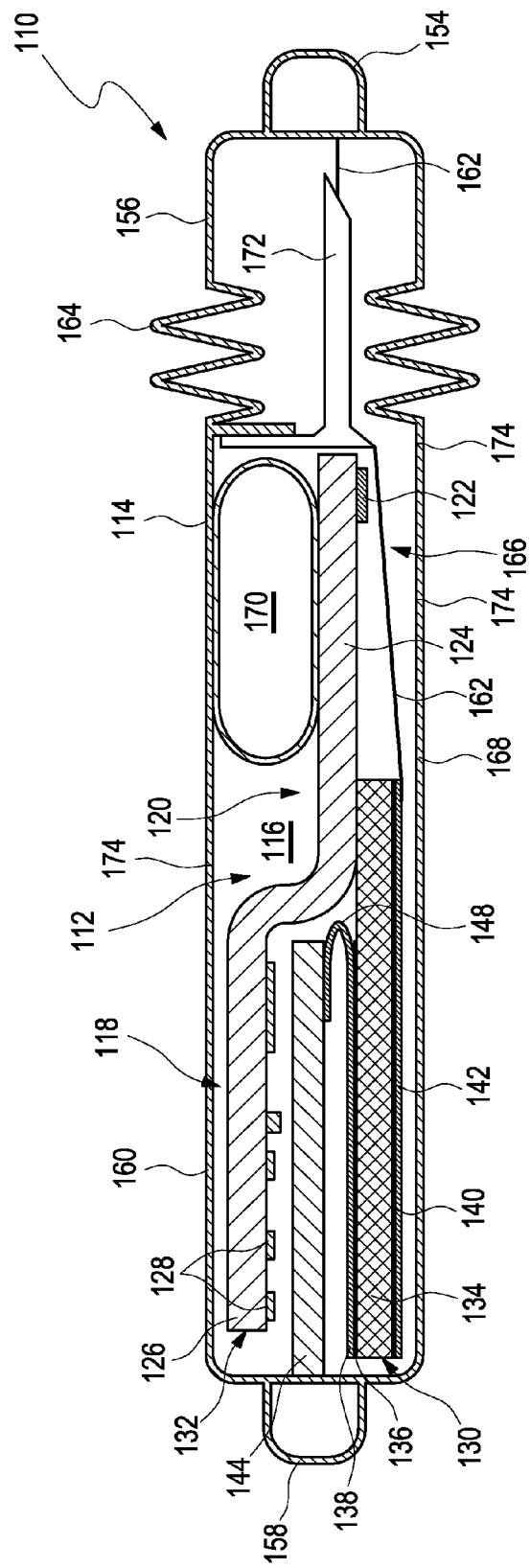
FIG. 5 shows a fourth exemplary embodiment of a sterilizing device and of a method.

In FIG. 1, a first exemplary embodiment of a sterilizing device 110 for sterilizing an implantable sensor 112 is shown in a schematic sectional representation. At the same time, the exemplary embodiment represented in FIG. 1 shows an example of a method for sterilizing the implantable sensor 112.

In general, as also in the present exemplary embodiment, the sterilizing device 110 may be designed as a sterile package and has a package 114, which is preferably designed such that it is sealed from bacteria and which has an interior space 116 and closes the latter such that it is sealed from bacteria. The implantable sensor 112 is accommodated in the interior space 116.

The implantable sensor 112 has an electronics part 118 and a sensor part 120, which is connected to the electronics part and can be implanted into a body tissue of a user. The sensor part 120 has at least one sensor electrode 122, generally 2, 3 or more sensor electrodes 122. These may be, in particular, enzymatic sensor electrodes 122, as described above. The at least one sensor electrode 122 may, for example, have been applied to a substrate 124. For example, this may be a plastics substrate 124, with a single-layered or multi-layered structure. For example, the substrate 124 may also be or include a flexible printed circuit board.

The sensor electrode 122 may be connected to the electronics part 118 via one or more supply leads that are not represented in FIG. 1. The electronics part 118 and the sensor part 120 may be formed in one piece, so that they preferably cannot be separated without being destroyed.

The electronics part 118 preferably likewise has at least one substrate 126. The substrate may be, for example, a leadframe. This leadframe is preferably in turn of a flexible design, for example in the form of a flexible printed circuit board. One or more electronic components 128 are arranged on and/or in the leadframe and/or the substrate 126. For example, these electronic components 128 may comprise one or more semiconductor components, in particular one or more active semiconductor components, such as for example amplifier components. In particular, the at least one electronic component 128 may comprise at least one potentiostat, which may be of a one-piece or multi-part form. The electronic components 128 may together form an activating and/or evaluating circuit of the implantable sensor 112. Furthermore, one or more interfaces may also be provided for communication of the implantable sensor 112 with one or more further components that are not represented.

In the exemplary embodiment represented, the implantable sensor 112, and here in particular the electronics part 118, are of a multi-part design and comprise at least a first part 130 and at least a second part 132. For example, the first part 130 may comprise at least one overlayer 134, which preferably later covers the electronic components 128. For example, the overlayer 134 may comprise a first adhesive layer 136, by means of which the overlayer 134 can be adhesively attached to the electronic components 128 and/or the substrate 126. In the initial state that is represented in FIG. 1, this first adhesive layer 136 may also be covered by a covering layer 138. This covering layer 138 may be pulled off later, before the adhesive attachment of the overlayer 134 to the substrate 126. The covering layer 138 may, for example, be designed as a protective film.

Furthermore, the overlayer 134 may have at least a second adhesive layer 140, on a side facing away from the substrate 126. By means of this second adhesive layer 140, which may generally also be replaced by any desired fixing element, the electronics part 118 can, for example, be fixed on the surface of the skin of a user of the implantable sensor 112, while the sensor part 120 has been or is completely or partially inserted through an insertion opening in a surface of the skin of a user into a body tissue of the user. The second adhesive layer 140 may also be covered by a covering layer 142, for example in turn by a protective film.

Furthermore, the sterilizing device 110 has at least one radiation shield 144. This radiation shield 144 may, for example, as represented in FIG. 1, be accommodated in the interior space 116. Alternatively, the radiation shield 144 may, however, also be entirely or partially accommodated outside the interior space 116, as a component part of the package 114 or as a separate component part.

The radiation shield 144 may, for example, be a metallic radiation shield, which is entirely or partially produced from at least one metallic material, in particular from at least one metallic solid material. For example, the radiation shield 144 may have a thickness d perpendicularly to an irradiating direction 146 that may be, for example, 1 to 10 mm, in particular, 5 mm. For example, the radiation shield 144 may comprise an aluminium plate.

In the case of a method for sterilizing the implantable sensor 112, first, in the state that is represented in FIG. 1, an irradiation of the sensor 112 may be performed, for the purpose of radiation sterilization, for example, by means of βradiation with an energy of 2.5 MeV. In particular, the implantable sensor 112 may in this case be exposed to a radiation dose of 25 kGy. Other types of radiation sterilization are also possible. The radiation sterilization is preferably performed in a directed manner, from one spatial direction or else, as described in more detail below, two, three or more spatial directions. During the radiation sterilization, the sensor part 120 and the first part 130 of the electronics part 118, that is to say the overlayer 134, are sterilized by the radiation sterilization. On the other hand, the radiation shield 144 shields the sterilizing radiation from the second part 132, which comprises the at least one electronic component 128 or at least one of the electronic components 128. For this purpose, the radiation shield 144 is preferably geometrically designed in such a way that reliable shielding of the second part 132, which comprises the at least one electronic component 128 or at least one of the electronic components 128, is ensured for all of the spatial directions of the sterilizing radiation that come into consideration. In particular, in this way all of the electronic components 128, or at least one or more of these electronic components 128, for example at least one sensitive component of the electronic components 128, can be shielded from the sterilizing radiation.

The package 114 may, for example, be entirely or partially designed as a plastics package. In particular, the package 114 may comprise a plastics sheeting. After the radiation sterilization, the package 114 may be handled in such a way that the first part 130 and the second part 132 are connected within the closed package 114, without opening of the package 114 being required. In particular, the overlayer 134 may thereby be applied to the at least one electronic component 128 and/or the substrate 126, for example be laminated on and/or adhesively attached. In order to accomplish this, the package 114 may, for example, be of a flexible design. In this case, the package 114 may, for example, be deformed in such a way that the radiation shield 144 is removed from the region between the first part 130 and the second part 132 and the second part 132 is applied to the first part 130. For example, an operator may grasp the left-hand end of the package 114 in FIG. 1 and the right-hand end of the package 114 and pull them apart directly after the sterilizing operation. In this design, the radiation shield 144 is preferably connected to the left-hand end of the package 114, so that, during the pulling apart, a deformation of the package 114 takes place in such a way that the radiation shield 144 is pulled out from the region between the first part 130 and the second part 132. As likewise represented as an option in FIG. 1, the radiation shield 144 may be connected to the covering layer 138, for example the protective film of the adhesive layer 136, by at least one connection 148. Accordingly, when the radiation shield 144 is being pulled out from the intermediate space between the first part 130 and the second part 132, the covering layer 138 may also at the same time be removed. Other designs are however also possible in principle, for example, separate removal of the covering layer 138 and/or a design without the covering layer 138 and/or without the first adhesive layer 136.

At the same time, the deforming process described above during the pulling apart of the package 114 allows the height of the package 114 in FIG. 1 to be reduced in such a way that the first part 130 and the second part 132 are pressed together. In this way, the implantable sensor 112 that is represented in FIG. 1 and is designed as a semifinished part can be turned into a usable implantable sensor 112, in which the overlayer 134 has been applied to the electronics part 118. All of the surfaces of the implantable sensor 112 that are facing the user have consequently been sterilized, without the electronic components 128 being damaged.

The sterilizing device 110 prepared in this way, according to FIG. 1, can then, for example, be delivered to a user. Alternatively, the pulling apart of the package 114 may also be performed by a user. A user may then, for example, open the package 114 and take possession of the implantable sensor 112 for use. In this case, the sensor part 120 can be completely or partially inserted into a body tissue, for example with an insertion aid which is likewise accommodated in the interior space 116, or which may be designed as a separate component, and is not represented in FIG. 1. The electronics part 118 may be completely or partially fixed onto a surface of the skin of the user by means of the second adhesive layer 140. For example, the covering layer 142 can be pulled off and the second adhesive layer 140 pressed onto the surface of the skin.

As discussed above, the final assembly of the implantable sensor 112 may be performed during the deformation of the package 114, which may, for example, be designed as a plastics sheeting, and in particular as a PE sheeting (PE: polyethylene). The package 114 may preferably remain closed during this deformation, so that the interior space 116 is still protected from re-contamination by the package 114. Alternatively, however, the package 114 may also be torn open during the deformation of the package 114, so that, for example, the removal of the radiation shield 144 and the final assembly of the implantable sensor 112 can be performed during opening of the package 114.

The adhesive layers 136, 140 may be designed, for example, as double-sided adhesive films. The second adhesive layer 140, facing the surface of the skin, may, for example, be designed as a flexible, breathable plaster.

The radiation shield 144 may preferably be produced from aluminium. Aluminium represents a good compromise with respect to absorption of electrons and a low braking radiation. However, it is also possible to use other materials, for example metallic materials. A composite of a light metal and a heavy metal may preferably be used, particularly preferably a composite of aluminium and lead, with, for example, the aluminium side facing the radiation source.

In FIG. 1, the electronics part 118 is only symbolically represented. In particular, the at least one electronic component 128 may also be arranged and/or designed in some other way than that represented in FIG. 1. Thus, as an alternative or in addition to the arrangement represented in FIG. 1, one or more electronic components 128 may also be arranged on the side facing the irradiating direction 146, be integrated in the substrate 126 and/or be arranged on an opposite side of the substrate 126, facing away from the irradiating direction 146. In turn as an alternative or in addition, the at least one electronic component 128 may also be completely or partially embedded in a substrate material, for example encapsulated with a synthetic resin, so as to produce a planar surface which can be adhesively bonded or in some other way connected well to the overlayer 134, and in particular the first adhesive layer 136.

In principle, it would also be possible to connect, for example encapsulate and/or permanently adhesively bond, the radiation shield 144 to the adhesive layer and the substrate 126 located thereabove and to the at least one electronic component 128 before the sterilization. Such a design would, however, result in principle in an undesirably high profile of the sensor system, since, with typical thicknesses of the radiation shield 144 of 5 mm, a high overall height of the electronics part 118 would be produced in the case of this design.

In FIG. 2, an alternative design of the sterilizing device 110 is shown in a representation analogous to FIG. 1. Accordingly, for the components represented, reference can initially be made largely to the description of FIG. 1.

In FIG. 2, however, an alternative, in which the radiation shield 144 is not accommodated in the interior space 116 but outside the interior space 116, is represented. The radiation shield 144 is consequently preferably not a component part of the package 114 but is formed separately from this package 114. For example, generally in the case of this exemplary embodiment or in other exemplary embodiments, the radiation shield 144 may however protrude into the interior space 116 in such a way that, before the final assembly of the implantable sensor 112, it is arranged in an intermediate space between the first part 130 and the second part 132. In this way, the radiation shield 144 may be arranged to shield sterilizing radiation that is impinging from one or more spatial directions and is not represented in the figure from the at least one electronic component 128, while the first part 130, for example the overlayer 134, is sterilized by the sterilizing radiation.

For example, the radiation shield 144 may protrude into the interior of the interior space 116 at at least one projection. For example, the package 114 may have at least one finger 150 protruding into the interior space 116, in the form of a pocket into which the radiation shield 144 is inserted and/or placed from the outside and/or into which the radiation shield 144 protrudes. The radiation shield 144 can be easily pulled out from the finger 150, in particular the pocket, after the radiation sterilization. For example, the radiation shield 144 may be fixedly connected to a production device. During an assembly of the sterilizing device 110 according to FIG. 2, the package 114 may, for example, be pushed with a pocket according to the invention or a finger 150 according to invention onto this radiation shield 144 and be pulled off again after the sterilization. This has the advantage that the radiation shield 144 can be used again and again.

As stated above, when the radiation shield 144 is being pulled out, the at least one covering layer 138 may also be pulled off from the first adhesive layer 136, for example in that a protective film is pulled off. For this purpose, a connection 148 may in turn be provided, for example, which in this case preferably does not directly connect the covering layer 138 to the radiation shield 144 but to the finger 150, in particular the pocket, into which the radiation shield 144 has been inserted. The finger 150 may be embodied in such a way that, when the radiation shield 144 is being pulled out, it is taken along with it and turned inside out. The covering layer 138, in particular the protective film, is then thereby also pulled off via the connection 148, and an adhesive connection between the first part 130 and the second part 132 is made possible.

The pulling out of the finger 150 during the removal of the radiation shield 144 may be made possible by a simple clamping region, as schematically represented in FIG. 3. Thus, FIG. 3 shows an optional design of the region of the finger 150 of the package 114. The exemplary embodiment shows that the finger 150, which may be designed in particular as a pocket protruding into the interior space 116, may have in particular a clamping region 152, at which the package 114 lies closely against the radiation shield 144. If the radiation shield 144 is pulled out from the finger 150, with the pulling direction to the left in FIG. 3, and/or if the package 114 is pulled from the radiation shield 144, with the direction of movement to the right in FIG. 3, the wall of the package 114 can bear firmly against the radiation shield 144 in the region of the clamping region 152, so that the finger 150 is pulled out from the interior space 116.

In FIG. 4, a third exemplary embodiment of a sterilizing device 110 is represented. The sterilizing device 110 may initially correspond in turn largely to the exemplary embodiment according to FIG. 1, so that with respect to most elements of this exemplary embodiment reference can be made to the above description of FIG. 1. In the state represented in FIG. 4, which is before and/or during the radiation sterilization, the first part 130 and the second part 132 of the implantable sensor 112 accommodated in the package 114 are in turn separated by the radiation shield 144. By analogy with FIG. 1, the irradiation may again be performed from below in FIG. 4, so that the first part 130 is radiation-sterilized, but the second part 132 is completely or partially shielded by the radiation shield 144.

In comparison with the exemplary embodiment in FIG. 1, the exemplary embodiment according to FIG. 4 has several modifications, which can be realized individually or in any desired combination.

Thus, the exemplary embodiment according to FIG. 4 first shows that the package 114 may have one or more grips. In the exemplary embodiment according to FIG. 4 there is provided a first grip 154, which is arranged at the right-hand end of the package 114 and which is connected to a first package part 156 of the package 114. A further grip 158, which is connected to a second package part 160 of the package 114, is provided at an end of the package 114 that is on the left in FIG. 4. By means of the grips 154, 158, the package parts 156, 160 can be pulled apart, preferably without the package 114 thereby being opened. The implantable sensor 112 is preferably connected to the first package part 156, for example, as represented by way of example in FIG. 4, via a pulling strip 162. This pulling strip may in principle act on any desired part of the implantable sensor 112, for example, as shown in FIG. 4, on the overlayer 134. Other designs are also possible.

During the radiation sterilization, the implantable sensor 112 is radiation-sterilized in the sterilizing device 110 according to the configuration shown in FIG. 4, for example with the irradiating direction 146 shown in FIG. 1. After the radiation sterilization, the package 114 can be stretched by grasping the package 114 at the grips 154, 158 and pulling the package parts 156, 160 apart. As this happens, for example, the radiation shield 144 is pulled out from the intermediate space between the first part 130 and the second part 132. In order to prevent tearing of the package 114, the first package part 156 and the second package part 160 may be connected by a bellows 164. As an alternative or in addition, however, the use of a package 114 of a flexible packaging material, for example, a flexible sheeting, is also conceivable.

FIG. 4 also shows an exemplary embodiment in which, during the deformation of the package 114 caused by the pulling apart of the grips 154, 158, the sensor is finally assembled, in that the first part 130 and the second part 132 are connected to each other. For the purpose of this final assembly, the implantable sensor 112 or parts of the same can be pulled through a constriction 166 in the package 114. This option is shown in FIG. 4. In this exemplary embodiment, the constriction is formed by way of example by an intermediate space between a wall 168 of the package 114 and a pressure pad 170. Other designs are also conceivable, for example designs with two or more pressure pads 170 and/or designs in which the constriction 166, for example a gap, is formed by other elements of the package 114. In the constriction 166, the first part 130 and the second part 132 can be pressed onto each other, so that, for example, the overlayer 134 is pressed onto the substrate 126 of the electronics part 118 and/or onto the electronic component 128, in particular by means of the first adhesive layer 136. In this way, a strength of the connection of the layered structure thereby produced can be increased significantly.

By means of the design shown in FIG. 4, particularly the sterile-sealed encapsulation can be retained during the final assembly of the implantable sensor 112. The provision of the grips 154, 158 allows convenient stretching of the package 114. As discussed above, instead of the bellows 164, which serve for the expansion of the package 114, a flexible package or some other kind of expandable package may also be used. However, sterile sealing during the deformation of the package 114 and the final assembly of the implantable sensor 112 is preferably retained for all of the designs of packages 114 of this kind.

It is possible by the pressure pad 170 that is integrated in the package 114 to exert pressure gently on the components of the implantable sensor 112, for example on the substrate 126, and particularly on the flexible printed circuit board. In particular, in this way the flexible printed circuit board can be electrically contacted and connected completely by the first adhesive layer 136. As an alternative or in addition to the pressure pad 170, other flexible and/or rigid and/or semirigid components may also be used.

To ensure a relative movement between the package 114 and the implantable sensor 112, the pulling strip 162 is preferably provided. This pulling strip 162 may, for example, extend between the grip 154 on the right and the overlayer 134. Other contact possibilities of such a pulling strip 162 are also possible. This pulling strip 162 should preferably be easy to remove. For example, the pulling strip 162 may therefore act on the covering layer 142 of the second adhesive layer 140, for example on the pull-off protective film. Other designs are also possible. As an alternative or in addition to the use of a pulling strip 162, another kind of connection may also take place between the package 114, in particular the first package part 156, and the implantable sensor 112. Thus, for example, a rigid or partially rigid package 114 may also be chosen, one which can interact mechanically with the implantable sensor 112 and in which an expandable region, for example in the form of the bellows 164, is positioned between a coupling of the package 114 to the implantable sensor 112 and a connection of the radiation shield 144 to the package 114.

Together with the pulling-off of the radiation shield 144 and the exposure of the first adhesive layer 136, one or more further assembly steps may also be completed within the package 114, steps in which the implantable sensor 112 and/or a sensor system comprising the implantable sensor 112 are finally assembled or further assembled. Such a design is shown by way of example in FIG. 5. The sterilizing device 110 represented there may initially correspond in turn by way of example to the design according to FIG. 4, so that reference can be made to the above description of FIG. 4. In principle, however, other designs are also possible.

In the exemplary embodiment represented in FIG. 5, in addition to the at least one implantable sensor 112, the interior space 116 of the package 114 also contains at least one medical aid, in this exemplary embodiment at least one insertion aid 172. As an alternative or in addition to the insertion aid 172, one or more medical aids designed in some other way may be accommodated in the package 114. The insertion aid 172 may, for example, be designed as a slit cannula or in some other way. Thus, it is generally necessary to implant the tip of the implantable sensor 112 with the sensor part 120 completely or partially subcutaneously. As stated above, a cannula, in particular a so-called slit cannula, with a slit extending along the longitudinal axis of the cannula, may be used as the insertion aid 172. The insertion aid 172, in particular the slit cannula, must in this case generally be sterilized in the same way as the tip of the implantable sensor 112. It is therefore generally advisable to perform the radiation sterilization jointly, and to carry out the bringing together of the components within the closed package 114. An appropriate embodiment of the package 114 allows this at least one assembly step to be carried out by the end user himself. As an alternative, however, this assembly may also be entirely or partially carried out by a manufacturer, since in many cases it may be advisable to carry out such a critical assembly step during production at the factory. In the case of the exemplary embodiment represented in FIG. 5 and of all other embodiments, the package 114 may in particular be of a completely or partially transparent design. Such a transparent design of the package 114 also offers the chance of carrying out a visual check on the assembly operation, and thereby ensuring that possible errors are discovered and eliminated.

As stated above, the package 114 may, in particular, be completely or partially produced from at least one sheeting element. For example, plastics sheetings, in particular flexible or stretchable plastics sheetings, such as for example PE sheetings and/or PET sheetings, may be used for this purpose. As an alternative or in addition, rigid materials may also be used for the package 114. For example, component parts of the package 114 may be designed as injection-moulded parts and/or as injection-blow-moulded parts or in some other way as plastics moulded parts. The moulded parts produced in such a way may, for example, have at least one opening, through which the sensor 112 can be introduced into the interior space 116. This at least one opening may be closed, for example, by a film and/or be connected to a film element and/or be closed by means of a flexible element, for example the bellows 164, or by means of a further packaging part, such as for example a stopper or a screw closure. For example, the package parts 156, 160 may be entirely or partially designed as plastics moulded parts which are connected via the bellows 164 and/or a flexible element designed in some other way.

For example, it may be advantageous in the case of the design according to FIG. 1 to design the package 114 completely as a sheeting element. In the case of other designs, such as for example in FIGS. 2 to 5, it may be advantageous to produce the package 114 as a rigid or semi-rigid formation, for example as plastic, in particular as a plastics moulded part, for example in an injection-moulding process or injection-blow-moulding process. Such a rigid package may have a large opening. The implantable sensor 112 can be placed in position through this opening. The opening may be closed with a suitable film, which after sterilization and final assembly exposes the opening again by being pulled off, and consequently makes the removal of the sterile implantable sensor 112 possible.

Embodying the package 114 completely or partially as a plastics moulded part generally also makes it possible for components to be precisely positioned and the sensor part 120 of the implantable sensor 112 and the insertion aid 172, for example the slit cannula, to be brought together in an error-free manner. The package 114 may also be embodied such that, in a first step, the assembly or positioning operations described above are performed, operations in which the at least two parts 130, 132 are brought together and assembled and/or in which the implantable sensor 112 is connected to the insertion aid 172, and, in a further step, the opening is performed in preparation for the removal of the sensor system with the at least one implantable sensor 112, and possibly the insertion aid 172. The two steps may also merge with each other and be performed within a single movement. For example, as stated above, the package 114 may comprise at least one predetermined breaking point. In FIG. 5, possible positions of the at least one predetermined breaking point are designated by way of example by the reference numeral 174. As an alternative or in addition, other positions of this predetermined breaking point 174 are also possible.

As indicated in FIG. 1, the radiation sterilization can generally be performed from one irradiating direction 146. However, this is not necessarily the case, since a number of irradiating directions may also be used in principle. This is represented by way of example in FIG. 6. The exemplary embodiment in FIG. 6 initially represents a combination of the exemplary embodiments in FIGS. 2 and 4, so that reference can be made to the above description of these FIGS. 2 and 4. Thus, the package 114 may, for example, in turn comprise a pressure pad 170, and also at least one deformable region, in particular a bellows 164. Furthermore, the package 114 may comprise at least one grip 154, in this case by way of example on a first package part 156. Other designs are also possible.

Figure 6:
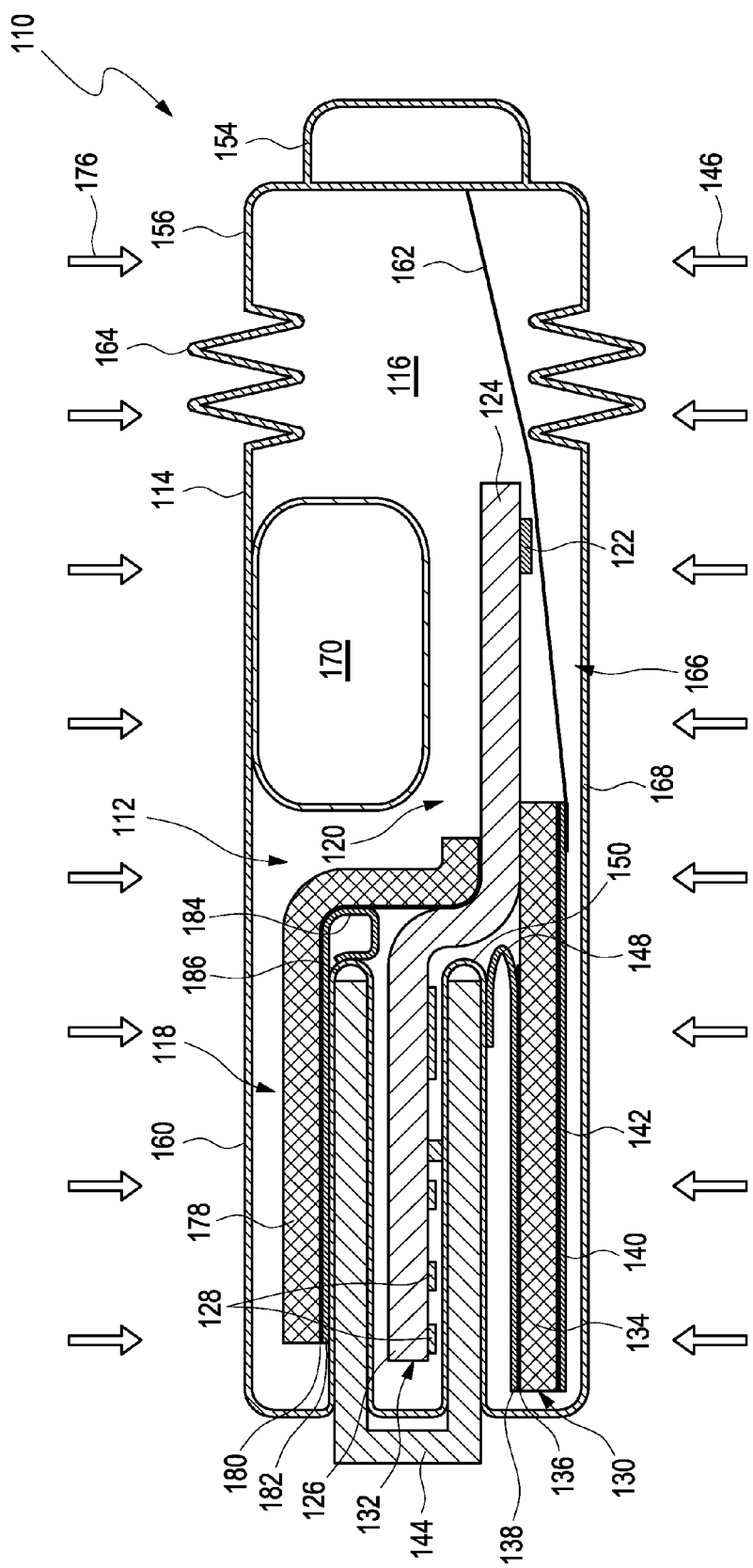
FIG. 6 shows a fifth exemplary embodiment of a sterilizing device and of a method.

By analogy with the exemplary embodiment according to FIG. 2, the implantable sensor 112 in FIG. 6 is in turn divided into a first part 130 and a second part 132, in particular in the region of the electronics part 118, the parts 130, 132 being radiation-sterilized in different ways. While the first part 132, which comprises the substrate 126 and one or more of the electronic components 128, is shielded by a radiation shield 144, the second part 132, which in this case is of a multi-part design, is radiation-sterilized. As a difference from the exemplary embodiment according to FIG. 2, in which the irradiation preferably takes place merely from one irradiating direction (not represented in FIG. 2), in FIG. 6 however irradiation takes place from both sides, from the irradiating direction 146 and a further irradiating direction 176. In this exemplary embodiment, the implantable sensor 112 can consequently be radiation-sterilized on both sides. The radiation shield 144 may in this case be designed in such a way that it shields the second part 132 from at least two spatial directions, for example in that the radiation shield 144 encloses the second part 132, as shown in FIG. 6. For example, the radiation shield 144 may be of a U-shaped configuration, as indicated in FIG. 6, the second part 132 of the implantable sensor 112 being arranged between the legs of the U during the radiation sterilization.

By analogy with the designs in FIGS. 1, 4 and 5, the radiation shield 144 may in this case in turn be arranged completely or partially in the package 114. As an alternative or in addition, however, as shown in FIG. 6 and by analogy with FIG. 2, the radiation shield 144 may also merely protrude into the package 114 and be designed such that it can be separated from the package 114. For example, for this purpose one or more fingers 150, 186 may in turn be provided, which protrude into the interior of the package 114 and into which the radiation shield 144 has been inserted. These fingers 150, 186 may generally in turn be formed as pockets similar to FIG. 2.

Thus, as shown in FIG. 6, the first part 130 has an overlay 134, with a first adhesive layer 136, which is covered by a covering layer 138. If, after the radiation sterilization, the finger 150 of the package 114 that is arranged between the overlayer 134 and the second part 132 is pulled out from the interior space 116, the covering layer 138 can be pulled off via a connection 148, and the overlayer 134 can be adhesively attached onto the at least one electronic component 128 and/or onto the substrate 126.

Furthermore, a further overlay 178 may also be applied to the substrate 126, for example to the flexible printed circuit board, from a side facing the further irradiating direction 176. This further overlay 178 can be radiation-sterilized from the irradiating direction 176, for example in a way analogous to the irradiating direction 146, for example in turn with βradiation within an energy of 2.5 MeV. The further overlayer 178 may, for example, in turn be provided with a further adhesive layer 180 and also a further covering layer 182. On a side facing the further overlayer 178, the package 114 may have at least one further finger 186, into which the leg of the radiation shield 144 that is facing the further overlayer 178 in the configuration shown in FIG. 6 protrudes. This further finger 186 may be connected to the further covering layer 182 by a further connection 184, so that, when the radiation shield 144 is being pulled out and when the finger 150, 186 is being pulled out, the covering layers 138, 182 are pulled off via the connections 148, 184.

During the radiation sterilization, the overlayers 134 and 178 are radiation-sterilized, whereas the substrate 126 and the at least one electronic component 128 are completely or partially shielded by the radiation shield 144. After the radiation sterilization, a final assembly of the implantable sensor 112 may be performed by a manufacturer and/or by a user of the implantable sensor 112, in that the package 114 is deformed. As this happens, the radiation shield 144 may optionally be pulled out from the package 114. As an alternative or in addition, however, the radiation shield 144 may also remain completely or partially in the package 114 similar to the designs in FIGS. 1, 4 and 5. Furthermore, during the deformation of the package 114, the final assembly of the implantable sensor 112 may be performed, for example by analogy with the exemplary embodiments described above, it optionally being additionally possible for assembly also to be performed with an insertion aid 172 that is not represented in FIG. 6 but is shown in FIG. 5. In turn, during the deformation of the package 114 in the final assembly, for example, the implantable sensor 112 may be pulled through at least one constriction 166 in the package 114, as indicated in FIG. 6. This may, for example, in turn be formed by a pressure pad 170. Other designs of the constriction that are described above are also possible. For example, a connection between the implantable sensor 112 and a first package part 156 may in turn take place for this purpose, for example in turn via a pulling strip 162. The action of the implantable sensor 112 being pulled through the constriction 166 allows the overlayers 134, 178 to be pressed from both sides onto the substrate 126, for example the flexible printed circuit board, and connected to it, for example via the optional adhesive layers 136, 180. In this way, an implantable sensor 112 can be produced, the outer surface of which is radiation-sterilized all around, but nevertheless radiation damage to the at least one electronic component 128 can be prevented during production by the radiation shield 144.

In general, by means of the designs described above of the present invention and/or with other designs according to the invention, commercially available electronic components can be used as electronic components 128 in spite of the necessary radiation sterilization with high-energy beams. The presented option of removal of the radiation shield 144 from the package 114 is accompanied by further advantages. Thus, for example, the radiation shield 144 no longer has to be delivered to a final consumer, which can bring about a cost saving and a reduction in the volume of the delivered product. In particular, the sensor system can have a low profile when it is used on the patient, since the radiation shield 144 is not a component part of the implantable sensor 112.

Furthermore, the possibility of integrating further medical aids into the package 114 that is indicated in FIG. 5 brings about additional advantages. Thus, for example, various components, such as the sensor part 120, in particular the sensor tip, the insertion aid 172, in particular the slit cannula, and the optional second adhesive layer 140, coming into contact with the skin, can be sterilized together in a package 114 designed as a sterile-sealed outer package and, after the sterilization, can be assembled together without opening the sterile package, for example in that these components are brought into one or more new relative positions within the package 114, in particular by deformation of the package 114.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF DESIGNATIONS

| | |
|---|---|
| 110 | sterilizing device |
| 112 | implantable sensor |
| 114 | package |
| 116 | interior space |
| 118 | electronics part |
| 120 | sensor part |
| 122 | sensor electrode |
| 124 | substrate |
| 126 | substrate |
| 128 | electronic component |
| 130 | first part |
| 132 | second part |
| 134 | overlayer |
| 136 | first adhesive layer |
| 138 | covering layer |
| 140 | second adhesive layer |
| 142 | covering layer |
| 144 | radiation shield |
| 146 | irradiating direction |
| 148 | connection |
| 150 | finger |
| 152 | clamping region |
| 154 | grip |
| 156 | first package part |
| 158 | grip |
| 160 | second package part |
| 162 | pulling strip |
| 164 | bellows |
| 166 | constriction |
| 168 | wall |
| 170 | pressure pad |
| 172 | insertion aid |
| 174 | predetermined breaking point |
| 176 | irradiating direction |
| 178 | further overlayer |
| 180 | further adhesive layer |
| 182 | further covering layer |
| 184 | further connection |
| 186 | further finger |

What is claimed is:

1. Method for sterilizing an implantable sensor for sensing at least one analyte in a body tissue, wherein the implantable sensor has at least one sensor part which can be introduced into the body tissue and has at least one sensor electrode for sensing the analyte and at least one electronics part, the electronics part having at least one electronic component and being connected to the sensor part, the method comprising:
   a) introducing the implantable sensor into at least one package, the package sealing the implantable sensor from bacteria and accommodating a radiation shield that shields the electronics part;
   b) irradiating the implantable sensor in the package with sterilizing radiation from at least one irradiating direction with electron radiation, the radiation shield shielding the electronic component of the electronics part from the sterilizing radiation, the radiation shield being arranged whereby the sensor part is sterilized by the sterilizing radiation.

2. The method of claim 1, wherein, after carrying out method step a), the implantable sensor has at least a first part and at least a second part, the first part being sterilized in method step b), the second part being shielded from the sterilizing radiation by the radiation shield in method step b), and wherein, after carrying out method step b), the method includes connecting the first part and the second part within the package.

3. The method of claim 2, the package being of a deformable design wherein when there is a deformation of the package after carrying out method step b), the first part and the second part are moved in relation to each other wherein the first part and the second part are connected to each other.

4. The method of claim 1 wherein the electronics part has a layered structure, the layered structure having at least one overlayer, wherein, in method step b), the overlayer is arranged relative to the radiation shield wherein the overlayer is at least partially sterilized by the sterilizing radiation, and wherein, after carrying out method step b), the overlayer is applied to the electronic component within the package without opening the package.

5. The method of claim 4 wherein the package has a deformable design and wherein deformation of the package moves the implantable sensor through at least one constriction, the overlayer being pressed onto the electronic component by the constriction.

6. The method of claim 5, wherein, during the deformation of the package, the radiation shield is separated from the package.

7. The method of claim 1 wherein, in method step a), at least one medical aid, the medical aid comprising at least one insertion aid, is additionally introduced into the package.

8. A sterilizing device for sterilizing an implantable sensor for sensing at least one analyte in a body tissue, the sterilizing device comprising:
   at least one implantable sensor for sensing the at least one analyte in the body tissue, wherein the implantable sensor has at least one sensor part which can be introduced into the body tissue and has at least one sensor electrode for sensing the analyte and at least one electronics part, the electronics part having at least one electronic component and being connected to the sensor part;
   at least one package, the package sealing the implantable sensor from bacteria and accommodating at least one radiation shield adapted to shield the electronic component of the electronics part during a radiation sterilization.

9. The sterilizing device of claim 8 wherein the sensor has at least a first part and at least a second part wherein the first part is sterilizable in the package during the radiation sterilization and the second part is shielded by the radiation shield during the radiation sterilization, the first part and the second part being connectable within the package after carrying out the radiation sterilization without opening the package.

10. The sterilizing device of claim 9 wherein the package has a deformable design wherein, during deformation of the package after carrying out the radiation sterilization, the first part and the second part are movable relative to each other whereby they are connected to each other.

11. The sterilizing device of claim of claim 8 wherein the electronics part has a layered structure, the layered structure having at least one overlayer, and wherein the package is configured such that, during the radiation sterilization, the overlayer is positioned relative to the radiation shield whereby the overlayer is at least partially sterilized by the sterilizing radiation while the electronic component is shielded by the radiation shield, the package being configured such that, after carrying out the radiation sterilization, the overlayer is attachable to the electronic component within the package without opening the package.

12. The sterilizing device of claim 11 wherein the package has a deformable design and is configured such that, when there is a deformation of the package, the implantable sensor is pulled through at least one constriction and the overlayer is pressed onto the electronic component by the constriction.

13. The sterilizing device of claim 12 wherein the package further comprises at least one finger protruding into an interior space of the packet wherein the radiation shield is insertable into the at least one finger from outside the interior of packet whereby, before the deformation of the package, the radiation shield can be inserted from the outside into at least one finger.

14. The sterilizing device of claim 13, the package having a deformable design wherein the implantable sensor is connected to a first package part of the package, the radiation shield being movable with a second package part of the package, the first package part and the second package part remaining connected to each other during deformation of the package such that a bacteria-sealed shielding of the implantable sensor is ensured.

15. The sterilizing device of claim 12, the package having a deformable design wherein the implantable sensor is connected to a first package part of the package, the radiation shield being movable with a second package part of the package, the first package part and the second package part remaining connected to each other during deformation of the package such that a bacteria-sealed shielding of the implantable sensor is ensured.

16. The sterilizing device of claim 12, wherein, during the deformation of the package, the radiation shield is separable from the package.

17. The sterilizing device of claim 16 wherein the package further comprises at least one finger protruding into an interior space of the packet wherein the radiation shield is insertable into the at least one finger from outside the interior of packet whereby, before the deformation of the package, the radiation shield can be inserted from the outside into at least one finger.

18. The sterilizing device of claim 16, the package having a deformable design wherein the implantable sensor is connected to a first package part of the package, the radiation shield being movable with a second package part of the package, the first package part and the second package part remaining connected to each other during deformation of the package such that a bacteria-sealed shielding of the implantable sensor is ensured.

19. Method for sterilizing an implantable sensor for sensing at least one analyte in a body tissue, wherein the implantable sensor has at least one sensor part which can be introduced into the body tissue and has at least one sensor electrode for sensing the analyte and at least one electronics part, the electronics part having at least one electronic component and being connected to the sensor part, the method comprising:
 a) introducing the implantable sensor into at least one package, the package sealing the implantable sensor from bacteria and accommodating a radiation shield that shields the electronics part; and
 b) irradiating the implantable sensor in the package with sterilizing radiation from at least one irradiating direction with electron radiation, the radiation shield shielding the electronic component of the electronics part from the sterilizing radiation, the radiation shield being arranged whereby the sensor part is sterilized by the sterilizing radiation;
 wherein, after carrying out method step a), the implantable sensor has at least a first part and at least a second part, the first part being sterilized in method step b), the second part being shielded from the sterilizing radiation by the radiation shield in method step b), and wherein, after carrying out method step b), the method includes connecting the first part and the second part within the package.

20. The method of claim 19, the package being of a deformable design wherein when there is a deformation of the package after carrying out method step b), the first part and the second part are moved in relation to each other wherein the first part and the second part are connected to each other.

21. Method for sterilizing an implantable sensor for sensing at least one analyte in a body tissue, wherein the implantable sensor has at least one sensor part which can be introduced into the body tissue and has at least one sensor electrode for sensing the analyte and at least one electronics part, the electronics part having at least one electronic component and being connected to the sensor part, the method comprising:
 a) introducing the implantable sensor into at least one package, the package sealing the implantable sensor from bacteria and accommodating a radiation shield that shields the electronics part; and
 b) irradiating the implantable sensor in the package with sterilizing radiation from at least one irradiating direction with electron radiation, the radiation shield shielding the electronic component of the electronics part from the sterilizing radiation, the radiation shield being arranged whereby the sensor part is sterilized by the sterilizing radiation;
 wherein the electronics part has a layered structure, the layered structure having at least one overlayer, wherein, in method step b), the overlayer is arranged relative to the radiation shield wherein the overlayer is at least partially sterilized by the sterilizing radiation, and wherein, after carrying out method step b), the overlayer is applied to the electronic component within the package without opening the package.

22. The method of claim 21 wherein the package has a deformable design and wherein deformation of the package moves the implantable sensor through at least one constriction, the overlayer being pressed onto the electronic component by the constriction.

23. The method of claim 22, wherein, during the deformation of the package, the radiation shield is separated from the package.

24. Method for sterilizing an implantable sensor for sensing at least one analyte in a body tissue, wherein the implantable sensor has at least one sensor part which can be introduced into the body tissue and has at least one sensor electrode for sensing the analyte and at least one electronics part, the electronics part having at least one electronic component and being connected to the sensor part, the method comprising:
 a) introducing the implantable sensor into at least one package, the package sealing the implantable sensor from bacteria and accommodating a radiation shield that shields the electronics part; and
 b) irradiating the implantable sensor in the package with sterilizing radiation from at least one irradiating direction with electron radiation, the radiation shield shielding the electronic component of the electronics part from the sterilizing radiation, the radiation shield being arranged whereby the sensor part is sterilized by the sterilizing radiation;

wherein, in method step a), at least one medical aid, the medical aid comprising at least one insertion aid, is additionally introduced into the package.

25. A sterilizing device for sterilizing an implantable sensor for sensing at least one analyte in a body tissue, the sterilizing device comprising:
   at least one implantable sensor for sensing the at least one analyte in the body tissue, wherein the implantable sensor has at least one sensor part which can be introduced into the body tissue and has at least one sensor electrode for sensing the analyte and at least one electronics part, the electronics part having at least one electronic component and being connected to the sensor part; and
   at least one package, the package sealing the implantable sensor from bacteria and accommodating at least one radiation shield adapted to shield the electronic component of the electronics part during a radiation sterilization;
   wherein the sensor has at least a first part and at least a second part wherein the first part is sterilizable in the package during the radiation sterilization and the second part is shielded by the radiation shield during the radiation sterilization, the first part and the second part being connectable within the package after carrying out the radiation sterilization without opening the package;
   further wherein the package has a deformable design wherein, during deformation of the package after carrying out the radiation sterilization, the first part and the second part are movable relative to each other whereby they are connected to each other.

26. A sterilizing device for sterilizing an implantable sensor for sensing at least one analyte in a body tissue, the sterilizing device comprising:
   at least one implantable sensor for sensing the at least one analyte in the body tissue, wherein the implantable sensor has at least one sensor part which can be introduced into the body tissue and has at least one sensor electrode for sensing the analyte and at least one electronics part, the electronics part having at least one electronic component and being connected to the sensor part; and
   at least one package, the package sealing the implantable sensor from bacteria and accommodating at least one radiation shield adapted to shield the electronic component of the electronics part during a radiation sterilization;
   wherein the electronics part has a layered structure, the layered structure having at least one overlayer, and wherein the package is configured such that, during the radiation sterilization, the overlayer is positioned relative to the radiation shield whereby the overlayer is at least partially sterilized by the sterilizing radiation while the electronic component is shielded by the radiation shield, the package being configured such that, after carrying out the radiation sterilization, the overlayer is attachable to the electronic component within the package without opening the package.

27. The sterilizing device of claim 26 wherein the package has a deformable design and is configured such that, when there is a deformation of the package, the implantable sensor is pulled through at least one constriction and the overlayer is pressed onto the electronic component by the constriction.

28. The sterilizing device of claim 27 wherein the package further comprises at least one finger protruding into an interior space of the packet wherein the radiation shield is insertable into the at least one finger from outside the interior of packet whereby, before the deformation of the package, the radiation shield can be inserted from the outside into at least one finger.

29. The sterilizing device of claim 28, the package having a deformable design wherein the implantable sensor is connected to a first package part of the package, the radiation shield being movable with a second package part of the package, the first package part and the second package part remaining connected to each other during deformation of the package such that a bacteria-sealed shielding of the implantable sensor is ensured.

30. The sterilizing device of claim 27, the package having a deformable design wherein the implantable sensor is connected to a first package part of the package, the radiation shield being movable with a second package part of the package, the first package part and the second package part remaining connected to each other during deformation of the package such that a bacteria-sealed shielding of the implantable sensor is ensured.

31. The sterilizing device of claim 27, wherein, during the deformation of the package, the radiation shield is separable from the package.

32. The sterilizing device of claim 31 wherein the package further comprises at least one finger protruding into an interior space of the packet wherein the radiation shield is insertable into the at least one finger from outside the interior of packet whereby, before the deformation of the package, the radiation shield can be inserted from the outside into at least one finger.

33. The sterilizing device of claim 31, the package having a deformable design wherein the implantable sensor is connected to a first package part of the package, the radiation shield being movable with a second package part of the package, the first package part and the second package part remaining connected to each other during deformation of the package such that a bacteria-sealed shielding of the implantable sensor is ensured.

* * * * *